United States Patent
Hockersmith et al.

(10) Patent No.: US 6,487,429 B2
(45) Date of Patent: Nov. 26, 2002

(54) USE OF TARGETED GLYCEMIC PROFILES IN THE CALIBRATION OF A NONINVASIVE BLOOD GLUCOSE MONITOR

(75) Inventors: Linda Hockersmith, Scottsdale, AZ (US); Thomas B. Blank, Chandler, AZ (US); Stephen L. Monfre, Gilbert, AZ (US); Timothy L. Ruchti, Gilbert, AZ (US)

(73) Assignee: Sensys Medical, Inc., Chandler, AZ (US)

(*) Notice: Subject to any disclaimer, the term of this patent is extended or adjusted under 35 U.S.C. 154(b) by 87 days.

(21) Appl. No.: 09/766,872

(22) Filed: Jan. 18, 2001

(65) Prior Publication Data

US 2002/0133063 A1 Sep. 19, 2002

Related U.S. Application Data

(60) Provisional application No. 60/208,027, filed on May 30, 2000.

(51) Int. Cl.[7] .................................................. A61B 5/00
(52) U.S. Cl. ........................................................ 600/316
(58) Field of Search ................................ 600/309, 310, 600/316, 319, 322, 347, 365; 250/252.1

(56) References Cited

U.S. PATENT DOCUMENTS

| | | | | |
|---|---|---|---|---|
| 5,068,536 A | * | 11/1991 | Rosenthal | 250/252.1 |
| 5,204,532 A | * | 4/1993 | Rosenthal | 250/252.1 |
| 5,209,231 A | * | 5/1993 | Cote et al. | 356/367 |
| 5,576,544 A | * | 11/1996 | Rosenthal | 250/252.1 |
| 5,666,956 A | * | 9/1997 | Buchert | 600/316 |
| 6,064,896 A | * | 5/2000 | Rosenthal | 600/316 |
| 6,157,041 A | * | 12/2000 | Thomas et al. | 250/339.09 |
| 6,168,563 B1 | * | 1/2001 | Brown | 128/904 |
| 6,309,884 B1 | * | 10/2001 | Cooper et al. | 356/39 |
| 6,333,501 B1 | * | 12/2001 | Labrenz | 250/339.09 |

* cited by examiner

Primary Examiner—Teresa Walberg
Assistant Examiner—Vinod D Patel
(74) Attorney, Agent, or Firm—Michael A. Glenn; Christopher Peil

(57) ABSTRACT

A method of calibrating a non-invasive blood glucose measurement instrument to a diabetic test subject employs targeted glycemic profiles in anti-correlated pairs. During calibration, reference blood glucose determinations are made using conventional invasive sampling methods. Concurrently, noninvasive spectral measurements are made using the noninvasive glucose monitor. Through controlled oral ingestion by the subject of calculated amounts of carbohydrate, the subject's blood glucose level is manipulated to mimic the patterns of the targeted profiles. During a first visit, a first profile of a pair is induced; during a second visit the inverse of the first profile is induced. The targeted profiles produce reference blood glucose values in which correlation to sampling factors is reduced or eliminated, thus the resulting calibration is correlated to glucose, and not to other analytes, sampling factors or environmental factors. A formula is provided for calculating the required amount of carbohydrate to ingest to induce a targeted glycemic profile in a test subject.

31 Claims, 11 Drawing Sheets

USE OF TARGETED GLYCEMIC PROFILES IN THE CALIBRATION OF A NONINVASIVE BLOOD GLUCOSE MONITOR

CROSS-REFERENCE TO RELATED APPLICATION

This application claims benefit of U.S. Provisional Patent Application Ser. No. 60/208,027, filed on May 30, 2000 and is a continuation-in-part of U.S. patent application Ser. No. 09/766,427, filed on Jan. 18, 2001, which claims benefit of U.S. provisional patent application Ser. No. 60/208,027, filed on May 30, 2000.

BACKGROUND OF THE INVENTION

1. Field of the Invention

The invention relates to non-invasive measurement of blood analyte levels. More particularly the invention relates to a process for calibrating a NIR spectrometer to a test subject using targeted glycemic profiles to obtain a wide range of reference blood glucose values, thereby increasing the robustness of the calibration and minimizing the possibility that the calibration is correlated to variables other than glucose.

2. Description of Related Art

NIR (near-IR) spectroscopy has long been studied for use in measurement of blood analytes, particularly glucose. The degree of physiologic and anatomical variation encountered in the general population has rendered it exceedingly difficult to develop an instrument that can be used to make blood glucose measurements on any subject. However, calibration of an instrument to a single individual is possible, and it produces measurements with sufficient accuracy to make the instrument clinically valuable. In general, the calibration process involves acquiring invasive glucose samples for reference values and concurrently making noninvasive spectral measurements. After the reference values and spectral data have been divided into a multivariate calibration set and a test set, used to insure accuracy of the calibration, a mathematical algorithm is developed that makes a blood glucose prediction from a new spectral sample.

It is desirable that the spectra making up the calibration set and test set, and subsequent sample spectra, be as free of noise from sampling factors as possible. For example, P. Cooper and T. Barker, Individual calibration of blood glucose for supporting noninvasive self-monitoring blood glucose (sic), PCT Application Ser. No. WO98/37805 (Feb. 26, 1997) teach a procedure for calibrating a noninvasive glucose monitor to an individual for self-monitoring of blood glucose levels. Spectroscopic samples are gathered at the subject's skin surface using a noninvasive glucose monitor. During sampling, the skin surface is repeatedly moved relative to the sampling probe, so that several samples are gathered, each from a slightly different measurement site. Then, a mean spectrum is calculated from the samples taken at the various sites. Thus, the influence on the spectral measurement of skin variability is minimized. At the same time, the subject's blood glucose level is measured using an invasive blood glucose-monitoring instrument. During the data-gathering phase of the calibration procedure, a glucose excursion is induced. Subsequently, blood sugar level is restored to basal level through the administration of exogenous insulin.

Moreover, it is essential that the reference glucose values do not correlate to any other sampling factor; for example skin temperature, skin humidity, room temperature, time, or other blood analytes. Cooper, et al. decorrelate to the various sampling factors by selecting a small fraction of up to sixty days worth of data with correlation constraints. While the teachings of Cooper, et al. recognize the importance of minimizing noise in the spectral data from various sampling factors, and provide strategies for such control, they do not address the need for an efficient calibration regimen, that can be accomplished in a short period of time.

Glucose excursions are often induced through the intravenous administration of dextrose, a disaccharide composed of two glucose subunits, during procedures commonly known as euglycemic insulin clamp techniques. Over the course of a procedure of this type, exogenous insulin may be infused at a rate that maintains a constant plasma insulin level above a fasting level. The glucose infusion is delivered via an indwelling catheter at a rate based on plasma glucose measurements done at five-minute intervals. When the plasma glucose level falls below basal level, the glucose infusion rate is increased to return plasma to basal levels. Conversely, glucose infusion is decreased or the insulin infusion increased when plasma glucose exceeds basal levels. The total amount of glucose infused over time, or the M value, comprises an index of insulin action on glucose metabolism. See Consensus development conference on insulin resistance, *Diabetes Care*, vol. 21 (2) p. 310 (1998). A typical profile resulting from this procedure would resemble a straight line, but a stepped increase or decrease in blood glucose may also be obtained. See Preservation of physiological responses to hypoglycemia two days after antecedent hypoglycemia in patients with IDDM, *Diabetes Care*, vol. 20 (8) p. 1293 (1997). Although euglycemic clamp studies are effective for quantifying the amount of insulin required to achieve a particular glycemic pattern, they suffer the disadvantage of being highly impractical in clinical settings. Additionally, they entail a significant amount of risk to the patient, and they generally meet with poor patient acceptance.

There exists, therefore, a need in the art for an efficient, low-risk method of calibrating a noninvasive glucose monitor to an individual patient that minimizes or eliminates correlation of reference glucose data to sampling factors such as skin temperature, skin humidity, room temperature, time, or other blood analytes. It would be advantageous to provide targeted, information rich, glycemic profiles for use in calibrating the noninvasive glucose monitor to individual subjects. It would be further advantageous to provide such glycemic profiles in pairs, in which one of the pair is anti-correlated to the other, so that the anti-correlated profiles are mirror images of each other. It would be a great advantage to provide a method of calibrating a noninvasive glucose monitor to a subject in which the subject's blood glucose level is dynamically manipulated through the controlled oral ingestion of calculated amounts of carbohydrate in such a manner as to reproduce the patterns of the anti-correlated profiles; during which time, noninvasive spectral measurements and determinations of blood glucose level would be made at regular intervals, thus degrading ancillary correlations to glucose and providing uncorrelated reference values for the calibration. Furthermore, it would be useful to provide a formula for reliably calculating the required amount of carbohydrate to produce a targeted glycemic profile in a test subject.

SUMMARY OF THE INVENTION

The invention provides a low-risk method of calibrating a noninvasive glucose monitor to an individual subject that minimizes or eliminates correlation of reference glucose data to sampling factors such as skin temperature, skin humidity, room temperature, time, or other blood analytes. Anti-correlated pairs of targeted glycemic profiles are provided, in which one profile of the pair is the inverse of the other. A formula is provided for calculating the amount of carbohydrate a subject must ingest orally in order to produce a glucose excursion that reproduces that of one of the target profiles. Advantageously, the formula employs a numerical index of a subject's sensitivity to carbohydrate challenges. Rapid-acting insulin is administered to lower blood glucose levels at a rate that duplicates that of a target profile. On successive calibration visits, first one profile of a pair and then the inverse profile are produced in a subject. Throughout the course of a visit, noninvasive spectral measurements are made at predetermined intervals. Concurrently, blood glucose levels are measured with a conventional, invasive blood glucose monitor. After the reference values and spectral data have been divided into a multivariate calibration set and a test set, used to insure accuracy of the calibration, a mathematical algorithm is developed that makes a blood glucose prediction from a new spectral sample. Thus, a calibration is provided that avoids correlating glucose to sampling factors.

In a preferred embodiment of the invention, anti-correlated target profiles are provided that include a single glucose excursion within a predetermined time period. In a second, equally preferred embodiment of the invention, each target profile includes multiple glucose excursions within a predetermined time period.

In addition, the calibration visits provide a valuable educational experience for diabetic subjects, providing them with a greater awareness of the impact of carbohydrate on blood glucose levels. Furthermore, since the invented formula reliably calculates the amount of carbohydrate required to produce a targeted response in a subject's blood sugar level, it serves as an important tool for dietary management of various disease conditions, such as diabetes and hypoglycemia.

DETAILED DESCRIPTION

Figure 1:
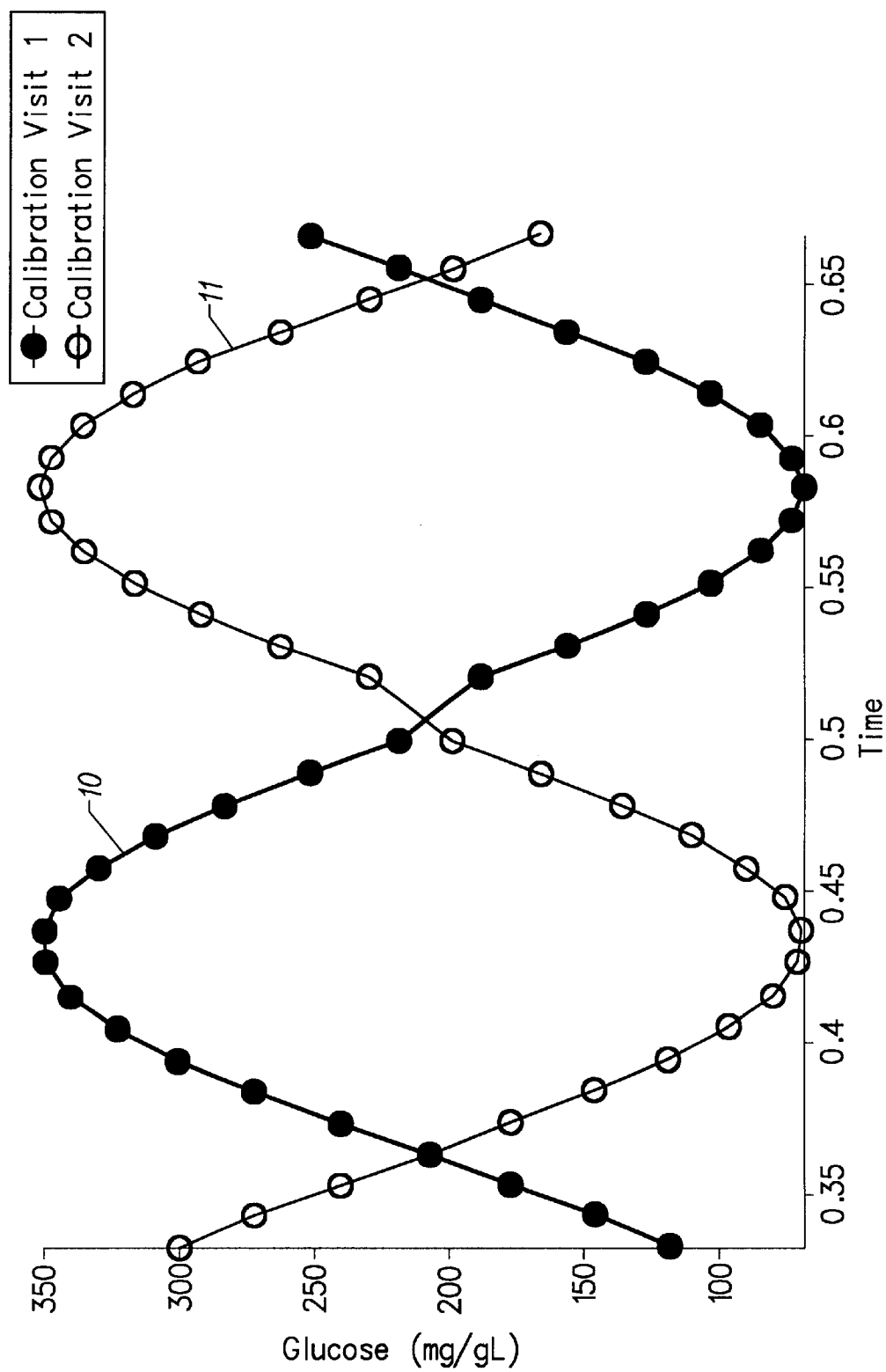
FIG. 1 shows a first pair of anti-correlated glycemic profiles, according to the invention.

Calibrating a noninvasive blood glucose monitor to an individual necessitates a calibration that is correlated only to blood glucose. Generating such a calibration requires reference blood glucose values that are uncorrelated to sampling factors such as skin temperature, environmental temperatures, time of day, and other blood analytes. FIG. 1 shows a pair of targeted, anti-correlated glycemic profiles 10, 11 in which one profile is the inverse of the other. The invention provides a method of calibrating a noninvasive blood glucose monitor using blood glucose reference values in which correlation to the sampling factors previously mentioned is greatly reduced or eliminated. In one embodiment of the invention, a test subject's blood glucose levels are actively controlled or manipulated through the oral ingestion of carbohydrate foods and the administration of rapid-acting insulin in such a way that the patterns of the targeted glycemic profiles of FIG. 1 are reproduced by the subject's own glycemic profile during successive calibration visits. Thus, since the subject's blood glucose level is under active control, the influence of other sampling factors on the reference values is greatly reduced or eliminated. By using anti-correlated profiles in separate calibration visits, the influence of factors that correlate across visits is reduced.

In general the various steps of the invented method are:

manipulating a subject's blood glucose level such that patterns of the profiles are reproduced by subject's own glycemic profile;

performing reference blood glucose measurements at predetermined intervals;

gathering non-invasive spectral measurements with a non-invasive glucose measurement instrument at said predetermined intervals; and generating a calibration that correlates reference measurements and spectral measurements, such that an algorithm predicts a blood glucose level from a new spectral sample.

Figure 2:
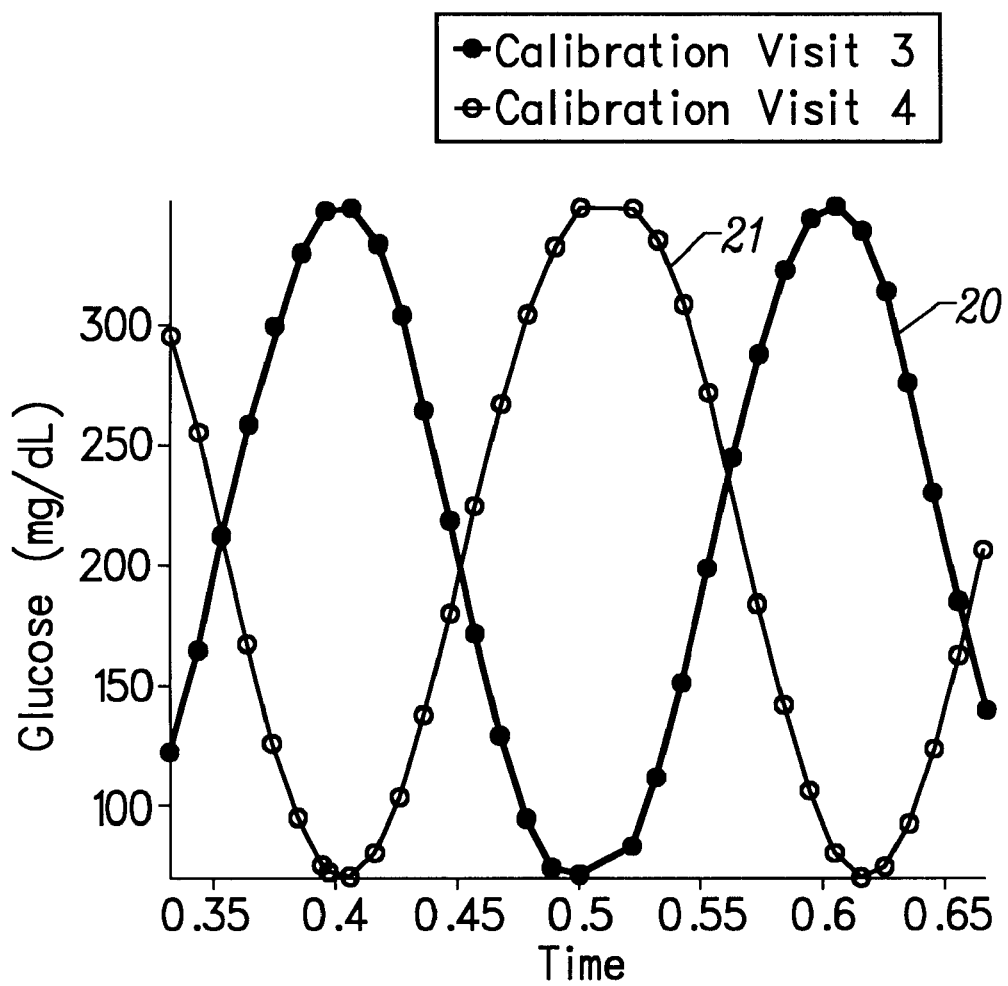
FIG. 2 shows a second pair of anti-correlated glycemic profiles, according to the invention.

In a preferred embodiment, the invention utilizes the targeted profiles of FIG. 1, involving a single glucose excursion. A subject makes two calibration visits, lasting approximately eight hours each. The first profile is produced on the first visit and the second profile is produced on a second visit. In an alternate, equally preferred embodiment, the invention utilizes the profiles shown in FIG. 2. The profiles 20, 21 involve multiple glucose excursions. As with the previous embodiment of the invention, two calibration visits are required. In a third, equally embodiment of the invention, the profiles of both FIG. 1 and FIG. 2 are employed in the calibration method. In this case, four calibration visits are required.

The preceding description is by way of example only, and is not intended to limit the invention. In addition to the embodiments described, other embodiments of the invention are possible. For example, the duration of the profiles is variable, and is not limited to the time durations previously described. While the previously described embodiments have employed sigmoidally patterned profiles, the permissible pattern of the profiles is highly variable. For example, profiles having concave or convex patterns may also be employed. The invention may also employ uncorrelated glycemic profiles, in addition to the anti-correlated profiles described above. While the previous embodiments have provided combinations of two and four profiles, in actual practice, the number of profiles required for a calibration is a function of the information content of the profiles employed. Therefore, the number is variable. The requirements for a target glycemic profiles are:

It must be information rich; that is, the values must exhibit a high degree of variation;

The variation must be uncorrelated to other sampling factors;

It must span a sufficient range of values to equal or exceed the target range of application; that is the range must equal or exceed the range of values encountered in the subject's day-to-day life.

The range of values needs to equal or exceed the sensitivity of the instrumentation.

Throughout the duration of each calibration visit, the subject's blood glucose level is measured at regular intervals using conventional invasive methods. Concurrently, noninvasive spectral measurements are taken.

The subject is fed either carbohydrate-rich meals to produce a glucose excursion, or low-carbohydrate meals to promote a drop in blood sugar level. The amount of carbohydrate to be ingested is calculated according to an inventive formula, described in greater detail below. The formula, based on a current glucose level, a target glucose level and the subject's sensitivity to carbohydrate, utilizes a novel numerical index to quantify carbohydrate sensitivity. Meals are composed of carefully selected, conventional foods and beverages. Orally ingesting carbohydrate in the form of conventional foods and beverages provides several important advantages. It provides a closer approximation of the subject's daily routine than conventional methods of inducing a glucose excursion do. In addition, ingesting the carbohydrate orally, rather than having it administered through intravenous infusion, as is often done, greatly diminishes any risk to the subject from the IV, and the glucose excursion resulting. Test subjects find the conventional foods and beverages to be much more palatable than the liquid glucose beverages often used to induce glucose excursions. The beverages, unpleasantly sweet, often induce nausea and even vomiting. While ingestion of the required amount of carbohydrate easily produces the required glucose excursion, a corresponding drop in blood sugar within the required time period requires the administration of insulin. Rapid-acting insulin, such as HUMALOG, produced by Eli Lilly & Co. of Indianapolis Ind. is employed to produce the necessary drop in blood sugar level.

The blood glucose reference values and the spectral measurements furnish a data set upon which the calibration is based. The data are first divided into a calibration data set and a test set. The reference values and the spectral measurements are correlated using commonly known multivariate techniques. An algorithm is generated, also using conventional analytical methods, based on the calibration data set, that predicts a blood glucose level from a new spectral measurement. The various aspects of the invention, particularly the method of producing targeted fluctuations in the subject's blood glucose level are described in greater detail below.

Experiment

A study was performed to determine if a targeted response in blood glucose level could be achieved from the oral ingestion of a calculated amount of carbohydrate in both Type 1 and Type 2 diabetic subjects. Use of a carbohydrate formula to calculate the required amount of carbohydrate would allow a low risk approach to obtaining a variety of predetermined glycemic profiles, which could subsequently be used to develop single subject glucose calibrations for noninvasive instrumentation.

In order to provide a broad range of reference glucose values, a target glucose profile for each calibration visit was specified as a glucose level range of from less than 90 mg/dL through a targeted high of greater than 300 mg/dL for each calibration visit, with a rate of change <5 mg/dl/minute. As previously explained, it was necessary to obtain data sets in which the patterns resulting from the blood glucose reference values did not correlate across calibration visits; in other words they were to be very dissimilar to each other. Therefore, the glycemic profiles were to be anti-correlated pairs, that is, one profile of a pair was to be the inverse of the other profile of the pair. During a first calibration visit, a glucose excursion that mimicked the first profile of a pair was to be achieved. The goal for a second visit was to achieve a glucose excursion that mimicked the second profile of the pair. Both calibration visits were eight hours in duration.

During the all-day calibration visits, the subjects were fed meals alternately composed of all carbohydrate or protein with non-digestible carbohydrate in order to achieve the recommended glucose profiles. The form of the carbohydrate was not limited, but was supplied both in the form of liquids and solid foods having a relatively low fat content. In addition, a rapid-acting insulin such as HUMALOG, manufactured by Eli Lilly and Co. of Indianapolis Ind., was employed to lower blood glucose levels, thus allowing the target profiles to be achieved in the allotted calibration time period.

Throughout each visit, non-invasive forearm scans were collected at fifteen-minute intervals using a near-infrared spectrometer instrument. Reference blood glucose measurements were done at the same time. For the invasive glucose determinations, capillary blood was collected from fingersticks and analyzed with a Hemocue Blood Glucose Analysis Instrument, manufactured by Hemocue AB of Ängleholm, Sweden.

The study participants were individuals diagnosed as having diabetes (Type 1 or 2) who were well controlled, having $HbA_1C$ (total glycosylated Hemoglobin) levels <7.5%. Table 1, below, provides demographic information on the subject pool.

TABLE 1

Subject demographics

| | Sex | DOB | Ethnicity | Diabetes Status | Year of Diagnosis | Health Status | Proteinuria | A1C |
|---|---|---|---|---|---|---|---|---|
| 1 | F | 6/10/58 | HIS | 2 | 1991 | Good | 1+ | 7.4 |
| 2 | M | 11/08/6 | CAU | 2 | 1994 | Good | Neg | 6.9 |
| 3 | M | 01/23/4 | CAU | 2 | 1993 | Good | Neg | 6.0 |
| 4 | F | 06/26/0 | CAU | 1 | 1982 | Good | Neg | 6.0 |
| 5 | M | 08/23/3 | CAU | 2 | 1998 | Fair | Neg | 6.1 |
| 6 | M | 05/07/6 | CAU | 2 | 1999 | Good | 1+ | 6.5 |
| 7 | M | 01/18/7 | CAU | 2 | 1996 | Good | 2+ | 5.5 |
| 8 | F | 02/24/4 | CAU | 1 | 1964 | Good | Trace | 7.5 |

TABLE 1-continued

Subject demographics

| | Sex | DOB | Ethnicity | Diabetes Status | Year of Diagnosis | Health Status | Proteinuria | A1C |
|---|---|---|---|---|---|---|---|---|
| 9 | F | 04/02/5 | HIS | 2 | 1994 | Good | Trace | 7.5 |
| 10 | F | 05/22/3 | CAU | 2 | 1998 | Good | Neg | 5.3 |

The formula used to calculate the amount of carbohydrate required to produce the desired glucose excursion is:

$$CHO = \frac{TARGET - STARTING}{X}, \quad (1)$$

where CHO is the amount of carbohydrate in grams, Target is the glucose level to be achieved, Starting is the current glucose level and X is a numerical index of the subject's sensitivity to carbohydrate challenge, described in greater detail below.

Table 2, below, shows a maximum and minimum, range and standard deviation of the glucose values for calibration visits of all clients. Maximum is the highest value achieved during a glucose excursion; minimum is a low value that may precede or follow a maximum value and the range is the span between maximum and minimum. As the results show, the target maximum and minimum values were achieved in ten out of twenty-three visits. Three subjects out of ten achieved the target range for visits one and two.

TABLE 2

Glucose statistics for visits 1, 2, and 3

| | | Entire Day | | | |
|---|---|---|---|---|---|
| Subject | Visit | Max | Min | Range | STD |
| 1 | 1 | 287 | 103 | 184 | 68.0 |
| 1 | 2 | 228 | 57 | 11 | 48.0 |
| 2 | 1 | 313 | 66 | 247 | 87.0 |
| 2 | 2 | 379 | 76 | 303 | 97.1 |
| 3 | 1 | 326 | 62 | 264 | 90.9 |
| 3 | 2 | 297 | 71 | 226 | 68.2 |
| 4 | 1 | 399 | 40 | 359 | 103.7 |
| 4 | 2 | 372 | 64 | 308 | 95.1 |
| 5 | 1 | 283 | 70 | 213 | 49.1 |
| 5 | 2 | 326 | 75 | 251 | 88.1 |
| 6 | 1 | 234 | 97 | 137 | 42.7 |
| 6 | 2 | 345 | 102 | 243 | 82.9 |
| 7 | 1 | 331 | 44 | 287 | 99.3 |
| 7 | 2 | 230 | 58 | 172 | 49.8 |
| 7 | 3 | 287 | 97 | 190 | 60.2 |
| 8 | 1 | 395 | 74 | 321 | 98.3 |
| 8 | 2 | 357 | 74 | 283 | 88.2 |
| 8 | 3 | 390 | 54 | 336 | 99.0 |
| 9 | 1 | 255 | 103 | 152 | 36.3 |
| 9 | 2 | 217 | 75 | 142 | 56.7 |
| 9 | 3 | 196 | 70 | 126 | 40.0 |
| 10 | 1 | 173 | 67 | 106 | 36.8 |
| 10 | 2 | 207 | 85 | 122 | 36.7 |

Figure 3:
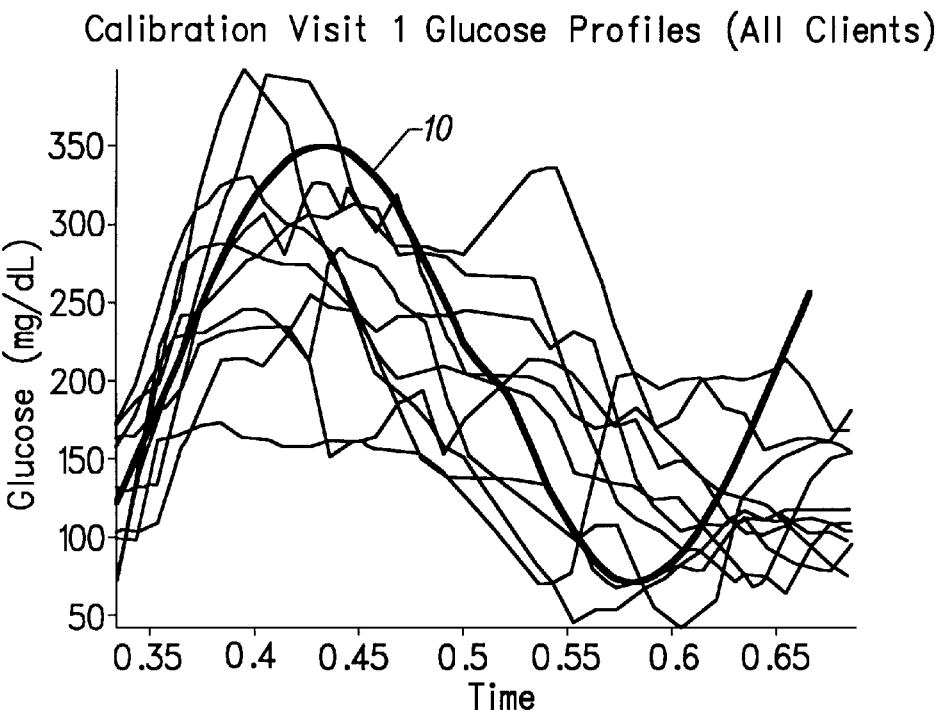
FIG. 3 shows a targeted glycemic profile for a first calibration visit superimposed on actual measured glycemic profiles from a subject pool, according to the invention.
Figure 4:
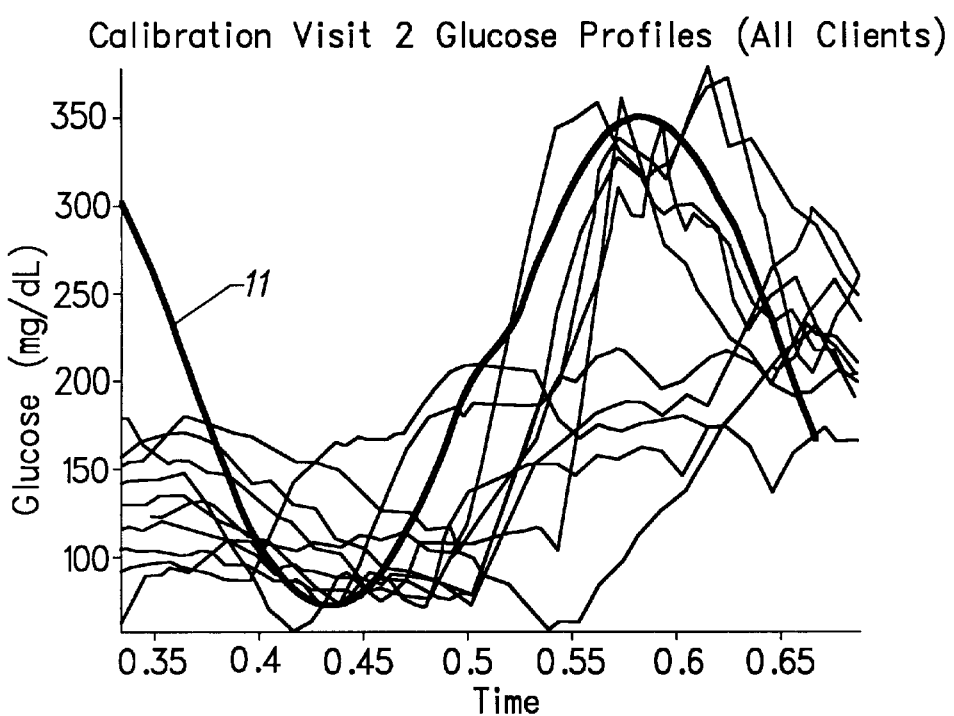
FIG. 4 shows a targeted glycemic profile for a second calibration visit superimposed on actual measured glycemic profiles from a subject pool, according to the invention.
Figure 5:
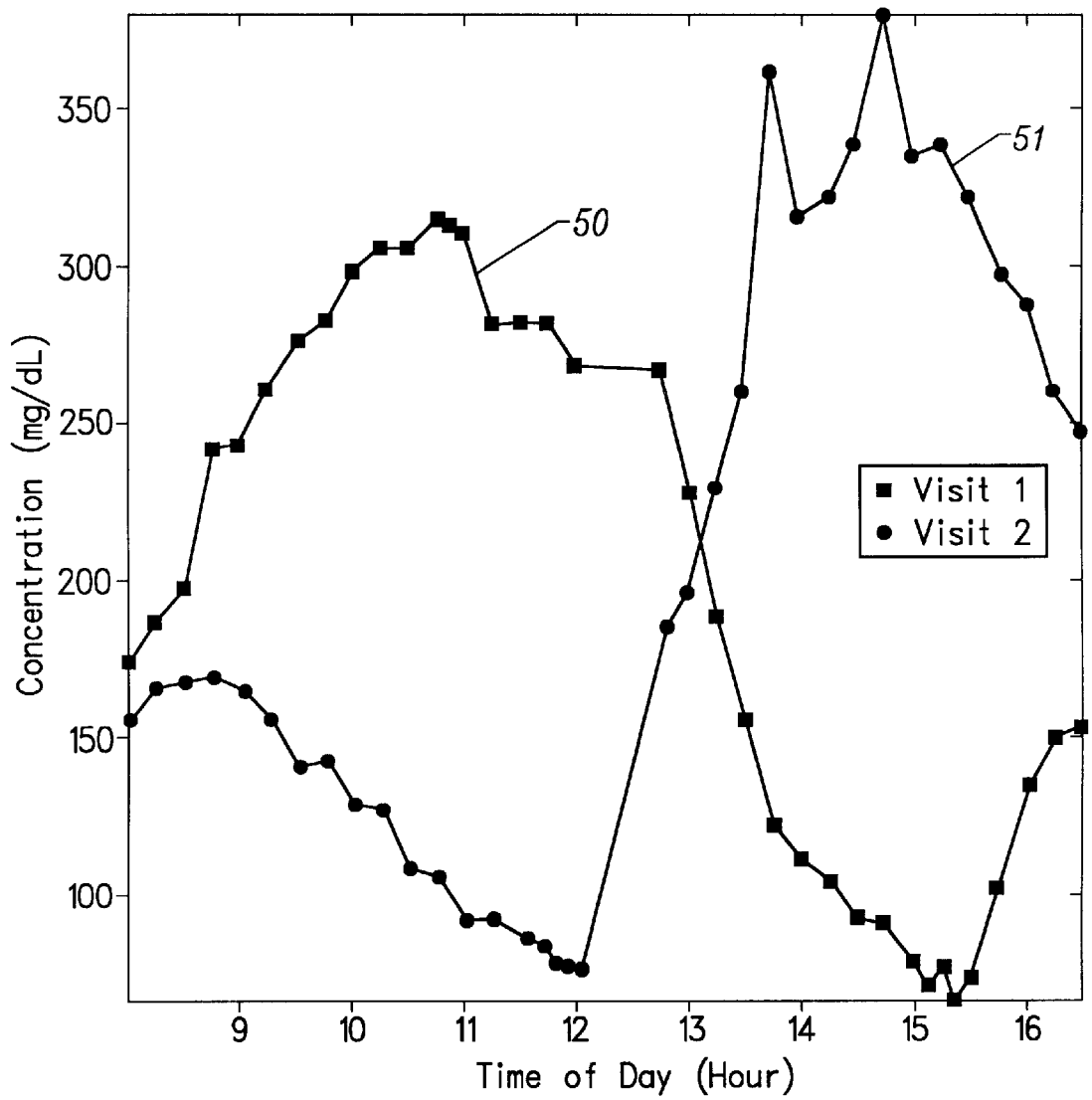
FIGS. 5–8 each show measured glycemic profiles for first and second calibration visits imposed on one another for first, second, third and forth subjects, respectively, according to the invention.
Figure 6:
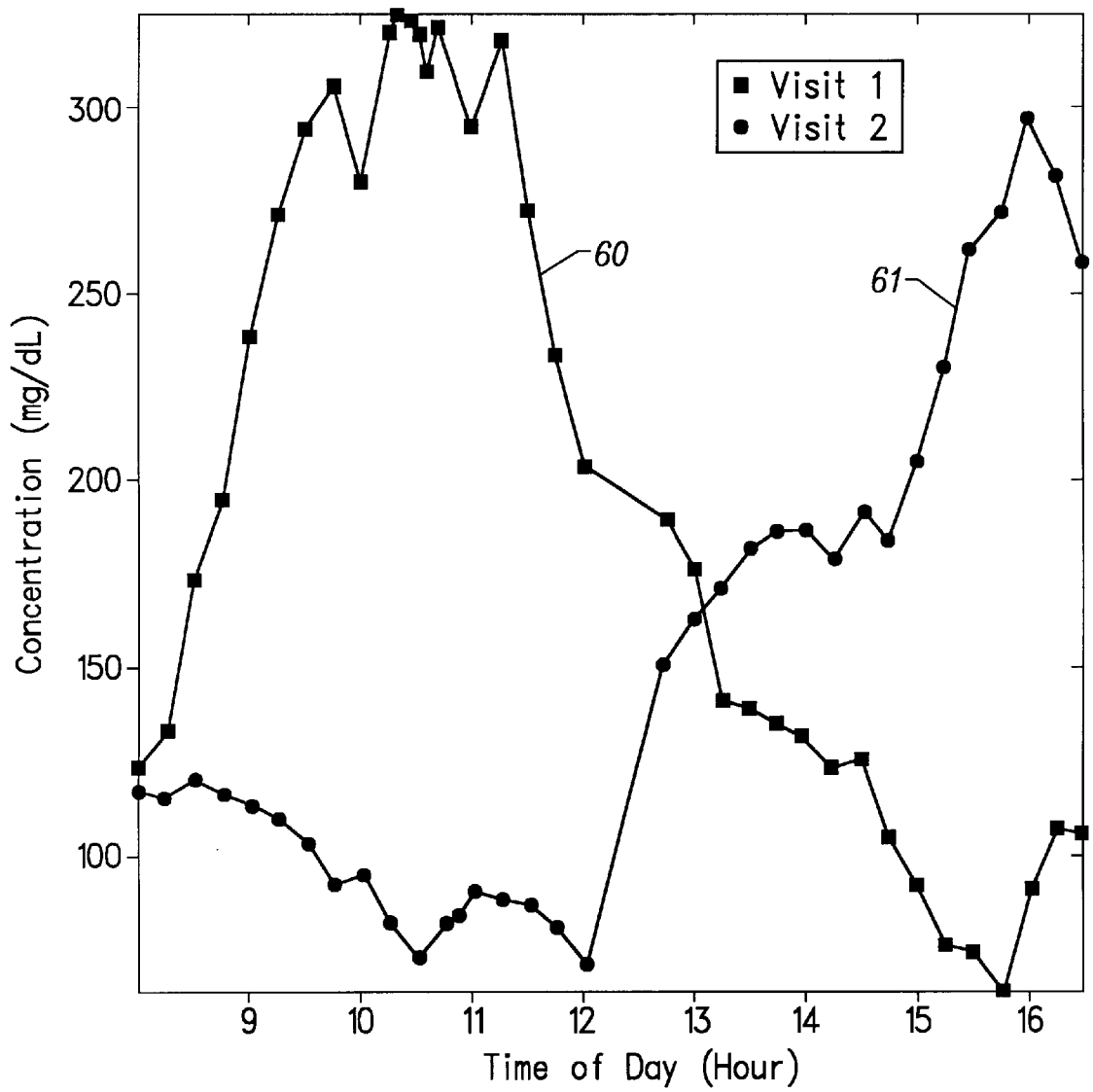
Figure 7:
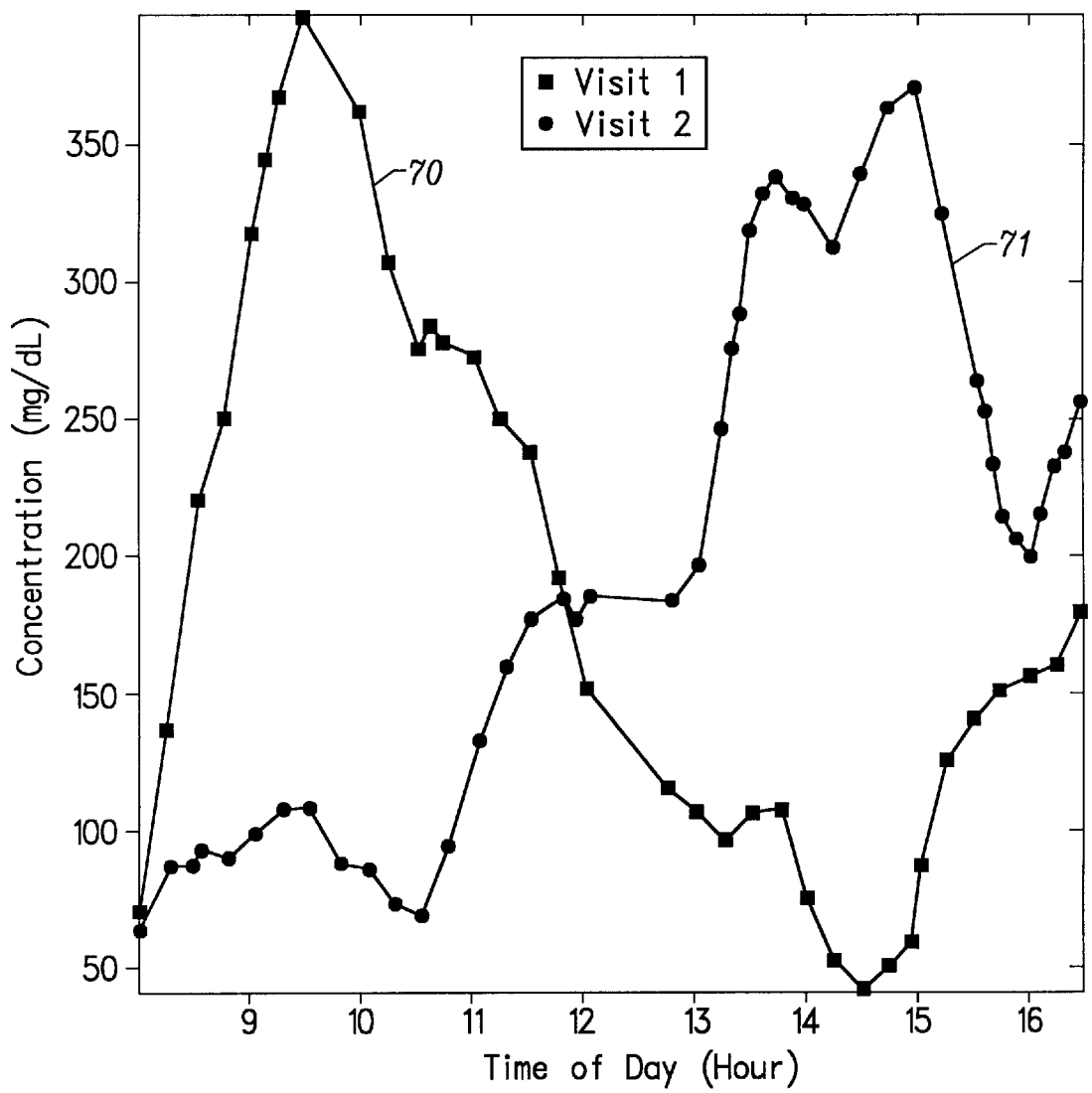
Figure 8:
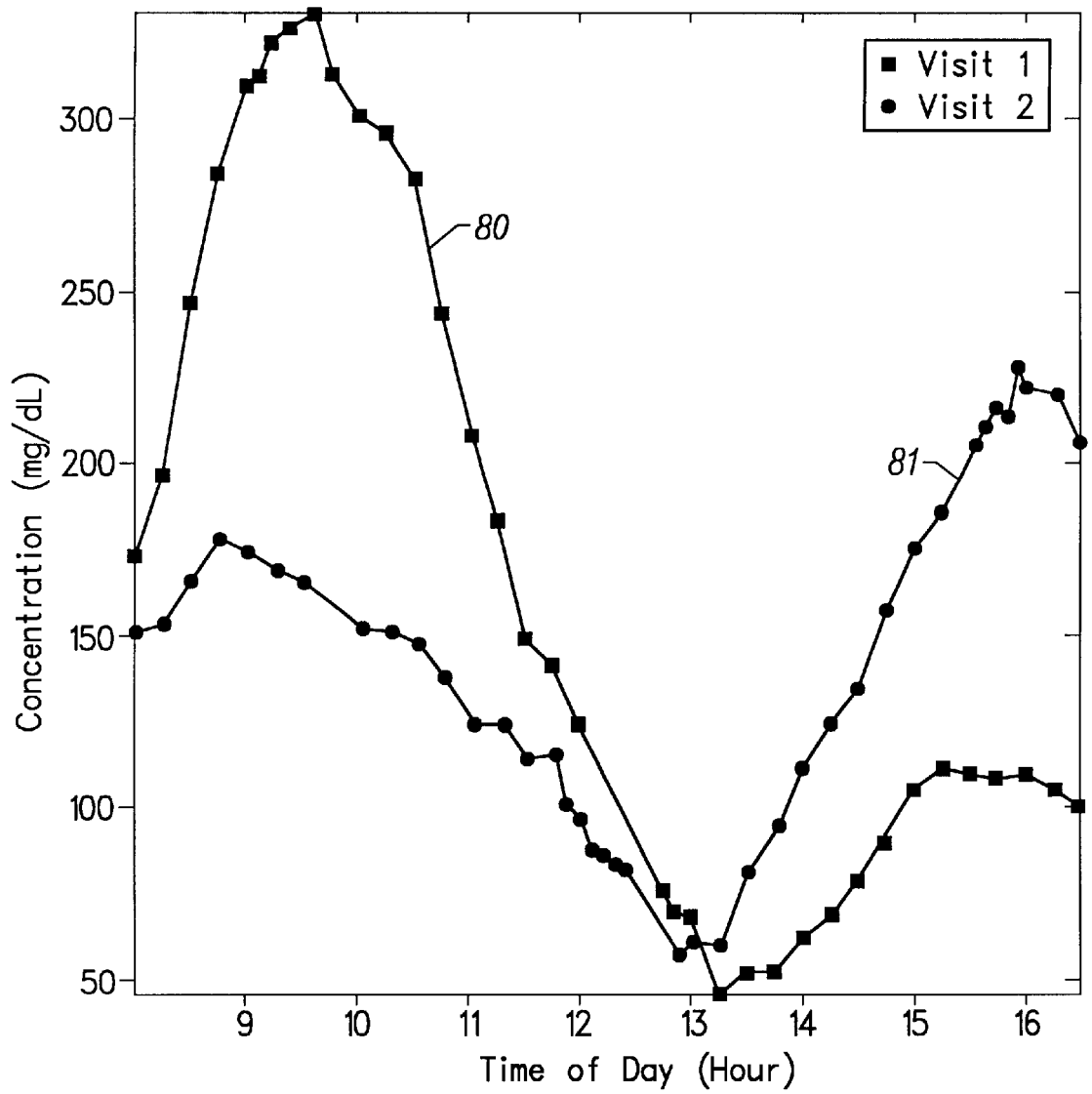
Figure 9:
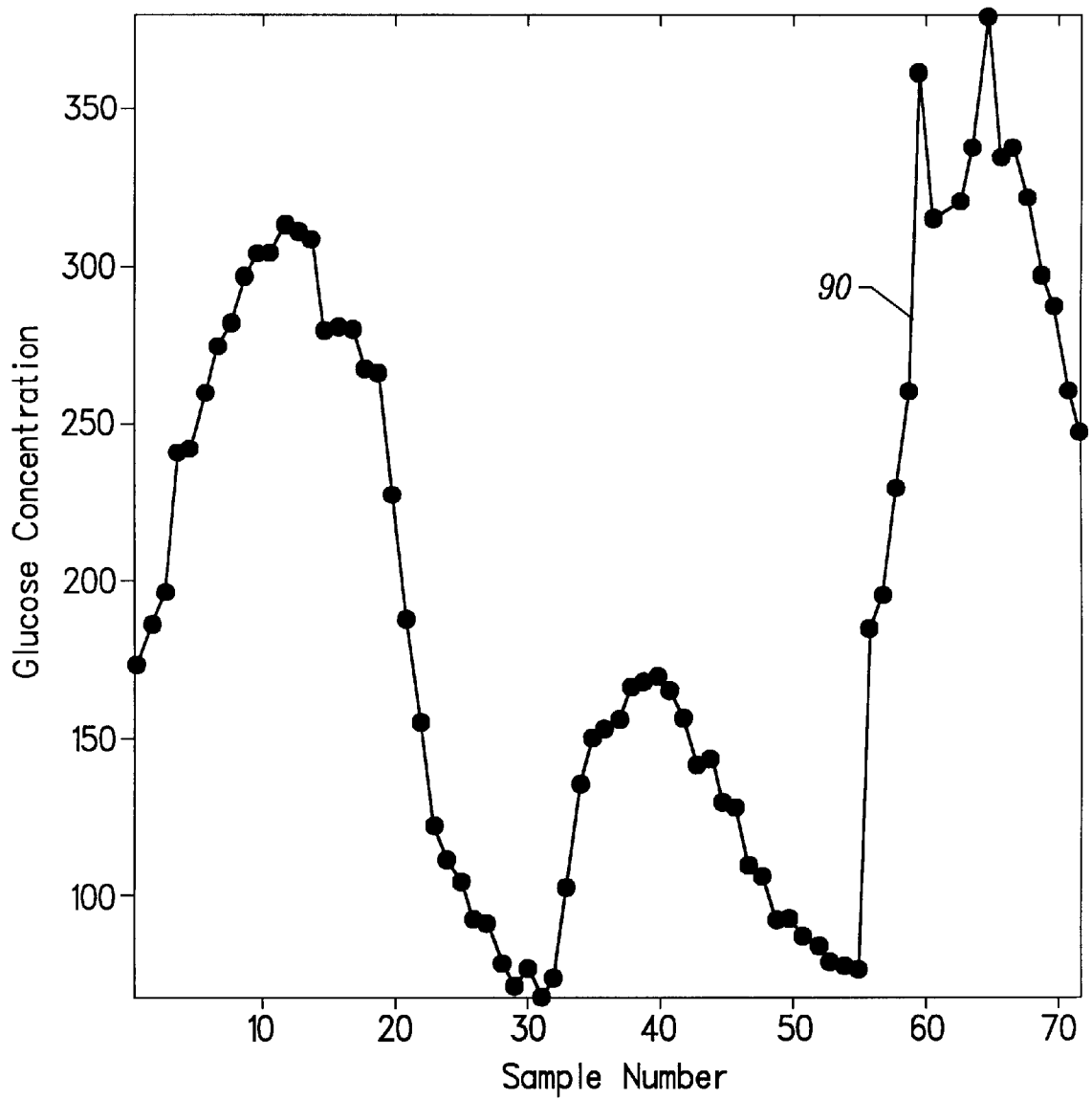
FIGS. 9–12 each show a measured glycemic profile for a third calibration visit for first, second, third and fourth subjects respectively.
Figure 10:
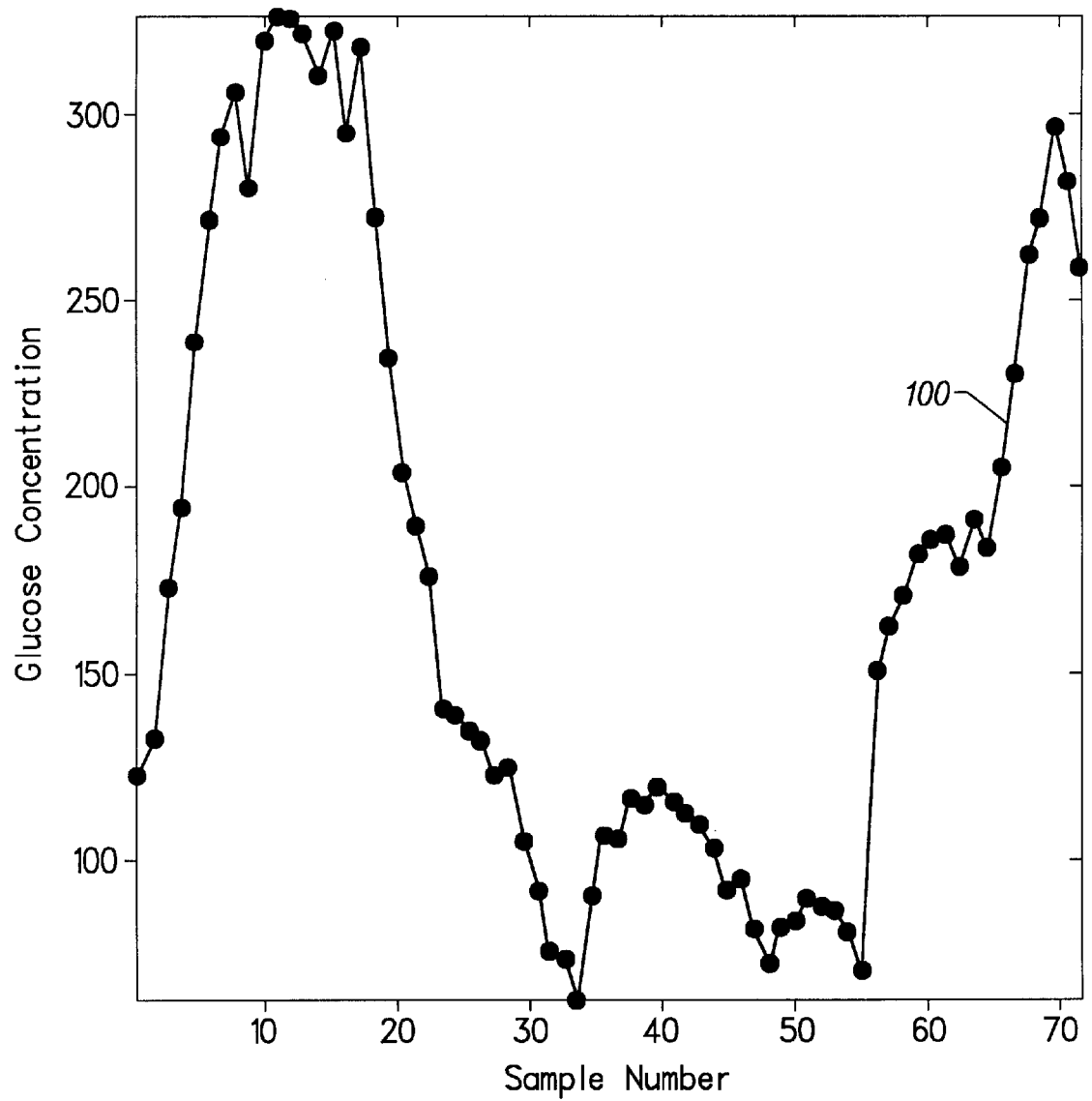
Figure 11:
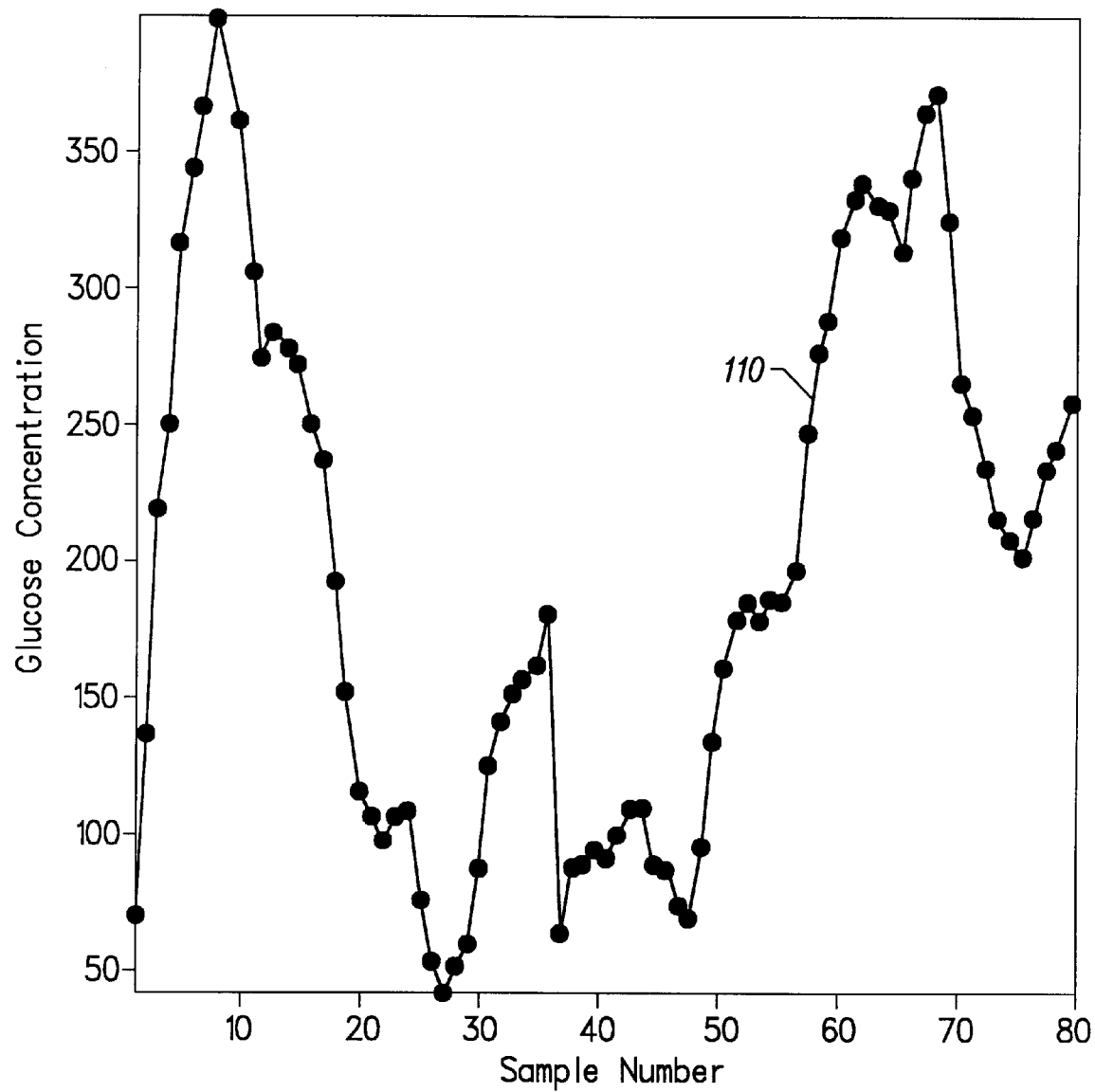
Figure 12:
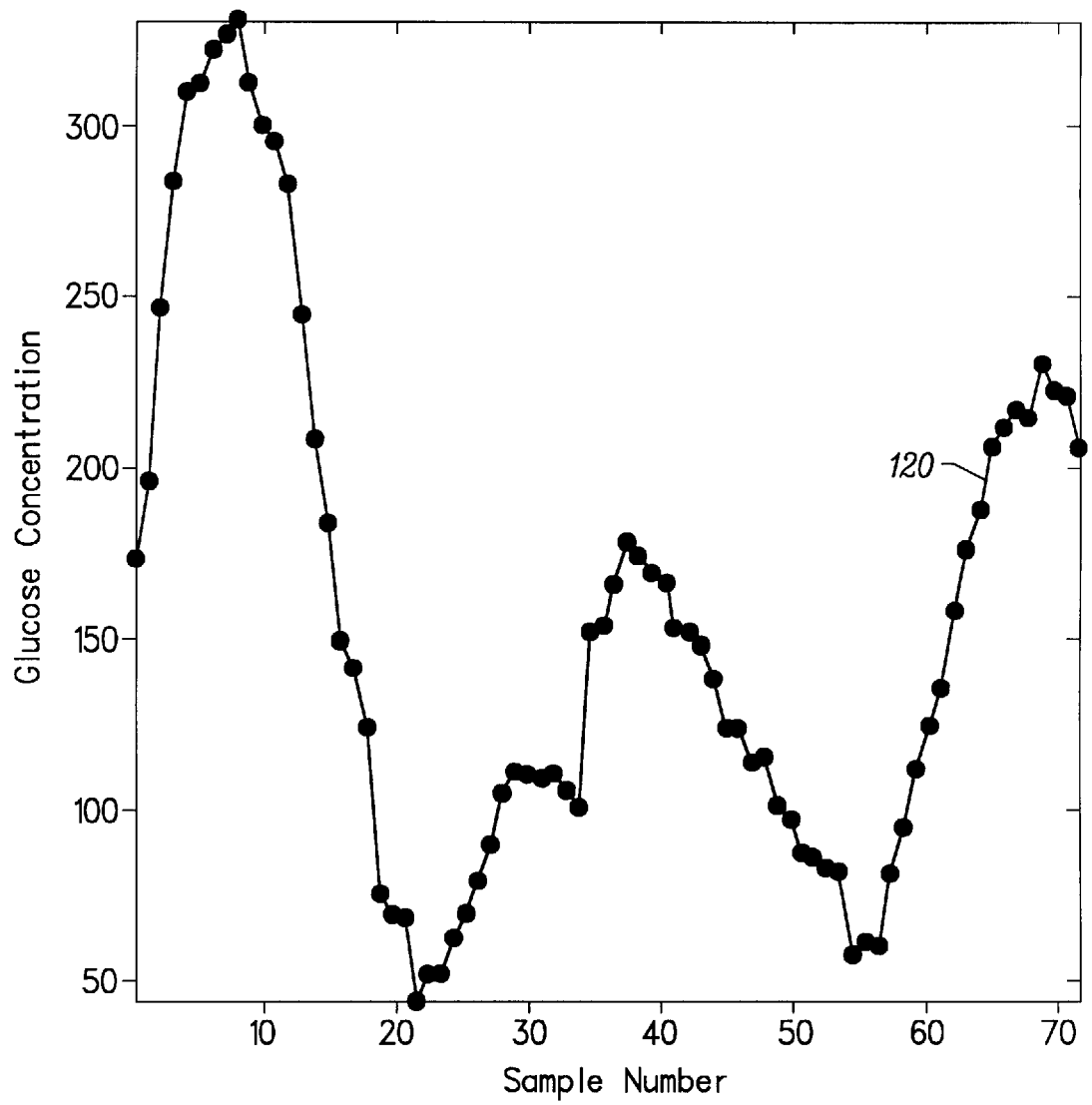

FIGS. 3 and 4 display the glucose profiles for each subject's calibration visit 1 and 2,respectively. The bold-faced curves represent the targeted glucose profiles 10, 11, for that visit. It is shown that the subjects' glucose levels were able to model the upward swing on both calibration visits. The were easily achieved with appropriate carbohydrate intake. The downward trends of the afternoons of calibration visit 1 and mornings of calibration 2 were achieved with less frequency than the upward trends. FIGS. 5 through 8 show the profiles of of four single subjects. For each subject, the profile for visit 1 50, 60, 70, 80 respectively and visit 2 51, 61, 71, 81 are imposed on each other.

As previously indicated, the rates of change for the downward trend were often less than those for the upward trend toward the maximum, even with the administration of exogenous insulin. FIGS. 9–12 show visit 3 profiles 90 100 110, 120 for the same four subjects. For the visit 3 profiles, a more agressive insulin-dosing regimen was employed to bring blood sugar levels down. It is apparent from the profiles that the more aggressive insulin-dosing regimen produces upward and downward rates of change that approximate each other more closely than those of visits 1 and 2.

The rate of change between the maximum glucose level and minimum glucose level was calculated for the first calibration visit (Table 2). This was calculated according to:

$$\text{Rate of change} = \frac{(\text{max glucose}) - (\text{min glucose})}{(\text{max time}) - (\text{min time})}. \quad (2)$$

The rate of change is expressed as milligrams per deciliter (mg/dl) over minutes. The rate of change is an indicator of a subject's capacity for the movement in blood glucose necessary to achieve the targeted glucose profile. The targeted glucose profile's rate of change is ±1.33 (mg/dl)/minute. For calibration visit one, the rate is a negative value, since it describes a downward trend. As Table 3, below, shows, three subjects (4, 5, and 6) had rates similar to that of the targeted profile.

Table 3 also shows the percentage of the visit that it took to achieve a fluctuation from a maximum to a minimum in the case of visit 1, or a minimum to a maximum in the case of visit 2, calculated according to:

$$\% \text{ of visit} = \frac{(\text{time at max glucose value}) - (\text{time at min glucose value})}{\text{ending time} - \text{initial time}} * 100. \quad (3)$$

TABLE 3

Rate of change from maximum to minimum glucose value and percent of visit spent fluctuating between maximum and minimum glucose levels during calibration visits 1 and 2.

| | Visit 1 | | Visit 2 | |
|---|---|---|---|---|
| Subject | Rate of change | % of visit | Rate of change | % of visit |
| TARGET | −1.33 | 43.8 | 1.33 | 43.8 |
| 1 | −0.58 | 62.1 | 0.48 | 70.66 |
| 2 | −0.89 | 54.4 | 1.86 | 32.14 |
| 3 | −0.81 | 64.0 | 0.95 | 47.13 |
| 4 | −1.20 | 59.1 | 0.74 | 82.24 |

TABLE 3-continued

Rate of change from maximum to minimum glucose value and percent of visit spent fluctuating between maximum and minimum glucose levels during calibration visits 1 and 2.

| Subject | Visit 1 | | Visit 2 | |
|---|---|---|---|---|
| | Rate of change | % of visit | Rate of change | % of visit |
| 5 | 1.42 | 29.7 | 2.11 | 23.68 |
| 6 | −0.34 | 79.5 | 0.96 | 52.30 |
| 7 | −1.30 | 43.4 | 0.95 | 35.59 |
| 8 | −0.80 | 79.5 | 1.90 | 29.49 |
| 9 | −0.24 | 71.3 | 1.06 | 26.53 |
| 10 | −0.40 | 53.0 | 0.82 | 29.40 |

This gives an indication of the amount of time over the visit for the subject to fluctuate between the maximum and minimum of their glucose profile. According to the target, the subject should require only 43.8% of the visit to travel between a maximum and a minimum in order to achieve the desired glucose profile during the first calibration visit. All, except Client 5 and 7, took more time to move from the maximum to minimum glucose value, not allowing for enough time to start the upward trend at the end of the first calibration visit.

The results indicate that administering a calculated amount of carbohydrate can be used to achieve anti-correlated glucose patterns. Type 2 individuals are less sensitive to carbohydrate excursion and require two to three times the amount of carbohydrate of that of Type 1 individuals.

The invented formula, represented as Equation 1, also provides the clinician with a method of quantifying the amount of carbohydrate necessary to achieve a desired blood glucose excursion in a diabetic subject. The formula takes into account the required glucose level to be achieved or the target, the current blood glucose level, or the starting value, and the sensitivity of the individual to carbohydrate.

'X' is a factor that serves as an index to carbohydrate sensitivity. The initial value is assigned by the clinician, according to type of diabetes and level of diabetes control, from a range of between 1 and 3, and is subsequently individualized to the subject. The amount of carbohydrate required to produce a target glucose excursion is calculated using a starting, generalized value of X, assigned by the clinician, as previously described. The diabetic subject then ingests the calculated amount of carbohydrate.

Blood glucose values are measured at regular intervals until the subject's blood glucose values reach a maximum. The actual maximum and the target maximum are compared and an individualized value of X, $X_i$ is calculated according to:

$$X_i = \frac{OBSERVED - STARTING}{CHO} \quad (4)$$

where 'OBSERVED' represents the observed maximum, as contrasted with the target maximum. Thus, for an individual, assigned an initial X value of 2, who attained a maximum of 297 mg/dl following ingestion of an amount of carbohydrate calculated to produce a maximum of 350 mg/dl, the individualized value of X, $X_i$, would be calculated as 1.7. This calculated value can be used by the subjects to further enhance their diabetes management. It can be assessed that the Type 1 clients (4 and 8) had a much higher sensitivity to carbohydrates (2.10 and 3.09, respectively) than the other clients. Table 4 below provides the sensitivity factors and Carbohydrate quantities employed for visit one profiles.

TABLE 4

CHO intake and sensitivity factor utilized in visit one profiles

| Subject | X | CHO intake | Glucose excursion |
|---|---|---|---|
| 1 | 0.99 | 145 | 144 |
| 2 | 0.64 | 216 | 139 |
| 3 | 0.83 | 246 | 203 |
| 4 | 2.10 | 156 | 328 |
| 5 | 0.48 | 260 | 125 |
| 6 | 0.37 | 274 | 102 |
| 7 | 1.23 | 128 | 157 |
| 8 | 3.09 | 75 | 232 |
| 9 | 0.61 | 246 | 151 |
| 10 | 0.38 | 196 | 74 |

The calibration visit also provide an educational experience for the diabetic subjects. The test indicate a greater awareness of the impact of carbohydrate foods on their blood glucose levels. Subjects who experience higher sensitivities may choose to move more of their carbohydrate food choices to the afternoon or evening where their medication regimen may produce lower sensitivities. Subjects report that their intake of carbohydrate is generally reduced, that they typically take smaller-sized portions of carbohydrate foods, and that nutritional information from food labels is more meaningful, all highly desirable outcomes in the management of diabetic conditions.

Furthermore, the invented formula and the individualized 'X' value may be used in the dietary management of any health condition where it is desirable to achieve and maintain an optimal glycemic profile. Those skilled in the art will appreciate other applications of the invented formula in general, along with applications of the general and individualized X values.

The absorption and, therefore, the activity of rapid-acting insulin are known to be highly individual. A further advantage of the invented methods is the capability of optimizing insulin injections relative to meal times. Review of blood test data generated during the calibration visits allows the individual's insulin response to be pinpointed easily. The time of injection is noted, and the point at which the glucose values begin to diminish is checked against the rate of change across intervals. When consistent patterns are observed, the onset of peak action can be verified.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

What is claimed is:

1. A method of calibrating a non-invasive blood glucose measurement instrument to an individual, said method comprising the steps of:

providing one or more targeted glycemic profiles;

manipulating said individual's blood glucose level such that patterns of said profiles are reproduced by subject's own glycemic profile;

performing reference blood glucose measurements at predetermined intervals;

gathering non-invasive spectral measurements with said non-invasive glucose measurement instrument at said predetermined intervals; and generating a calibration that correlates said reference measurements and said spectral samples, such that an algorithm predicts a blood glucose level from a new spectral sample.

2. The method of claim 1, wherein said profiles are uncorrelated to sampling factors other than glucose level.

3. The method of claim 1, wherein a total range of values of each of said profiles equals or exceeds a total range of values encountered in application.

4. The method of claim 1, wherein a total range of values of each of said profiles equals or exceeds instrument sensitivity.

5. The method of claim 1, wherein a single one of said profiles is uncorrelated to any other single one of said profiles.

6. The method of claim 1, wherein said profiles are provided in at least one anti-correlated pair.

7. The method of claim 6, wherein a pattern of one profile from said pair of profiles is an inverse of a pattern of a remaining profile from said pair.

8. The method of claim 7, wherein said pattern from said first profile is reproduced in said individual's glycemic profile in a first calibration visit.

9. The method of claim 8, wherein said pattern from said second profile of said pair is reproduced in said individual's glycemic profile in a second calibration visit.

10. The method of claim 9, wherein a calibration visit is approximately eight hours in duration.

11. The method of claim 1, wherein said patterns of said anti-correlated glycemic profiles degrade ancillary correlations to glucose that may occur between calibration visits.

12. The method of claim 11, wherein said ancillary correlations include any of: time and temperature.

13. The method of claim 1, wherein said profiles move blood glucose levels up and down quickly to prevent said calibration from being correlated to variables other than glucose.

14. The method of claim 13, wherein said profiles include maximum and minimum values, a maximum value comprising a peak blood glucose value and a minimum comprising a minimum blood glucose value occurring in relation to said maximum.

15. The method of claim 14, wherein a rate of change of said subject's blood glucose level is calculated according to:

$$\text{rate of change} = \frac{(\text{max glucose}) - (\text{min glucose})}{(\text{max time}) - (\text{min time})}.$$

16. The method of claim 15, further comprising the step of calculating peak insulin activity based on said rate, said maximum and said minimum.

17. The method of claim 1, wherein said step of manipulating said individual's blood glucose profile comprises the steps of:

calculating a required amount of carbohydrate to ingest to effect an increase in blood glucose level from a starting value to a target value according to the formula:

$$CHO = \frac{TARGET - STARTING}{X},$$

where CHO represents said required amount of carbohydrate, and wherein X comprises an index representing said individual's sensitivity to carbohydrate; and orally ingesting said required amount of carbohydrate by said individual.

18. The method of claim 17, further comprising the step of calculating said individual's insulin response, wherein said rate of change comprises an indicator of onset of peak activity of exogenous insulin.

19. The method of claim 17, wherein a percentage of a calibration visit required for said individual's blood glucose level to fluctuate from maximum to minimum level is calculated according to:

$$\% \text{ of visit} = \frac{(\text{time at max glucose}) - (\text{time at min glucose})}{\text{ending time} - \text{initial time}} * 100.$$

20. The method of claim 17, wherein said carbohydrate comprises any of:

liquid food;

solid food; and liquid and solid food.

21. The method of claim 17, wherein X is a generalized value selected from a range of approximately 1 to 3.

22. The method of claim 17, wherein said manipulating step further comprises the step of:

administering low-carbohydrate meals to effect a decrease in said individual's blood glucose level.

23. The method of claim 17, wherein said manipulating step further comprises the step of:

administering insulin to effect a rapid decrease in said individual's blood glucose level.

24. The method of claim 1, wherein said step of performing reference blood glucose measurements comprises the steps of:

drawing blood samples; and analyzing said blood samples for glucose using a blood glucose analyzer.

25. The method of claim 1, wherein said non-invasive glucose measurement instrument comprises a Near IR spectrometer instrument.

26. The method of claim 1, wherein said predetermined intervals are approximately fifteen minutes in length.

27. The method of claim 1, wherein said step of generating said calibration comprises the steps of:

creating a calibration data set and a test data set from said reference blood glucose values and said spectral measurements, wherein said blood glucose values are correlated to said spectral measurements;

generating an algorithm based on said calibration data set and said test set that predicts a blood glucose value from a new spectral measurement.

28. The method of claim 1, wherein said individual is human.

29. The method of claim 1, wherein said individual is diabetic.

30. The method of claim 1, wherein said providing step comprises:

providing a pair of said targeted profiles.

31. The method of claim 1, wherein said providing step comprises:

providing a two pairs of said targeted profiles.

* * * * *